United States Patent [19]

Djuric et al.

[11] Patent Number: 4,791,133
[45] Date of Patent: Dec. 13, 1988

[54] PHENYLENE, FURYL, AND THIENYL LEUKOTRIENE B4 ANALOGUES

[75] Inventors: Stevan W. Djuric, Glenview; Richard A. Haack; Julie M. Miyashiro, both of Chicago, all of Ill.

[73] Assignee: G. D. Searle & Co., Chicago, Ill.

[21] Appl. No.: 67,526

[22] Filed: Jun. 26, 1987

[51] Int. Cl.$^4$ .................... A61K 31/38; A61K 31/34; C07D 211/08; C07D 409/00; C07D 333/22; C07C 69/76; C07C 59/48; C07C 103/26

[52] U.S. Cl. .................... 514/438; 514/210; 514/317; 514/326; 514/422; 514/428; 514/461; 514/471; 514/532; 514/570; 514/571; 514/622; 546/192; 546/212; 546/214; 548/517; 548/527; 548/530; 548/953; 548/964; 548/966; 549/77; 549/79; 549/496; 549/501; 560/55; 562/470; 564/170

[58] Field of Search .................... 549/79, 498, 501, 77, 549/496; 562/470; 564/170; 514/438, 461, 570, 571, 622, 210, 326, 317, 422, 428, 471, 532; 560/55; 548/964, 966, 953, 517, 527, 530; 546/192, 212, 214

[56] References Cited

U.S. PATENT DOCUMENTS

| 4,053,466 | 10/1977 | Yoshimira et al. | 549/79 |
| 4,304,783 | 12/1981 | Beck et al. | 549/79 |
| 4,309,407 | 1/1982 | Lautenschlager | 549/79 |
| 4,546,194 | 10/1985 | Miyano . | |
| 4,638,011 | 1/1987 | Das | 549/79 |

FOREIGN PATENT DOCUMENTS 1040735  9/1966  United Kingdom ................ 562/470

OTHER PUBLICATIONS

Biochem and Biophys. Res. Comm., 138, 540–546, (1986).
Lewis et al., J. Clin. Inves., 73, 889–897, (1984).
Bray, Brit. Medical Bull., 39, 249–254, (1983).

Primary Examiner—Alan Siegel

Attorney, Agent, or Firm—Mary Jo Kanady; Paul D. Matukaitis

[57] ABSTRACT

This invention relates to leukotriene B4 antagonists having the structure

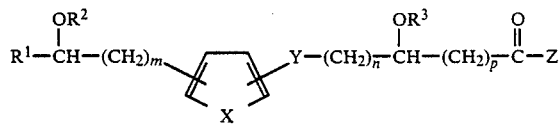

and the pharmaceutically acceptable addition salts thereof;

wherein $R^1$ is lower alkyl having 1–10 carbon atoms; or lower alkenyl or alkynyl having 2–10 carbon atoms; or lower alkadienyl having 3–10 carbon atoms; or lower alkadiynyl or alkenynyl having 4–10 carbon atoms;

wherein $R^2$ and $R^3$ are the same or different and represent hydrogen or lower alkyl having 1–6 carbon atoms;

wherein X is CH=CH, S, or O;

wherein Y is CH=CH or C≡C;

wherein Z is $OR^4$ or $NR^5R^6$, and wherein $R^4$ represent H, lower alkyl having 1–6 carbon atoms, or a pharmaceutically acceptable cation, and wherein $R^5$ and $R^6$ act independently and represent H or lower alkyl having 1–6 carbon atoms, or $R^5$ and $R^6$ may act together with N to form a cycloamine of the formula:

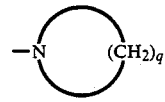

wherein q is an integer from 2–5;
wherein m and n are the same or different and either 1 or 0; and
wherein p is an integer from 1 to 5.

24 Claims, No Drawings

PHENYLENE, FURYL, AND THIENYL LEUKOTRIENE B4 ANALOGUES

BACKGROUND OF THE INVENTION (a) Field of the Invention

The present invention relates to pharmaceutical agents (compounds) which act as leukotriene B4 (LTB4) antagonists in mammals. The compounds of the present invention are useful in treating inflammatory conditions in mammals such as psoriasis, Crohn's disease, ulcerative colitis and the like.

(b) Prior Art

LTB4 (Formula I) is an arachidonic acid metabolite which is an important mediator of inflammation in mammals. As a mediator of inflammation, LTB4 is known to induce chemotaxis, chemokinesis, aggregation, and degranulation of leukocytes in vitro, and to induce accumulation of polymorphonuclear leukocytes, and increase vascular permeability and edema formation in vivo.

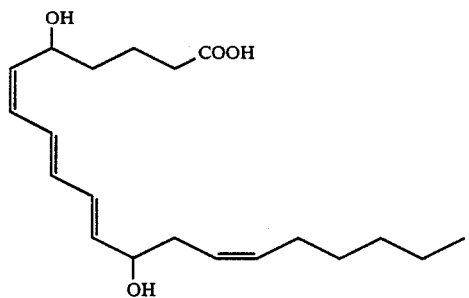

Particularly high levels of LTB4 are detected in lesions in inflammatory diseases such as rheumatoid or spondylarthritis, gout, psoriasis, ulcerative colitis, Crohn's disease, and some respiratory diseases.

Accordingly, it is an object of this invention to produce compounds for use as pharmaceutical agents which will exhibit LTB4 antagonist activity in mammals.

A potential LTB4 antagonist (Formula II), which is structurally different from the compounds of the present invention, is disclosed in Biochem. and Biophys. Res. Comm., 138 540-546 (1986).

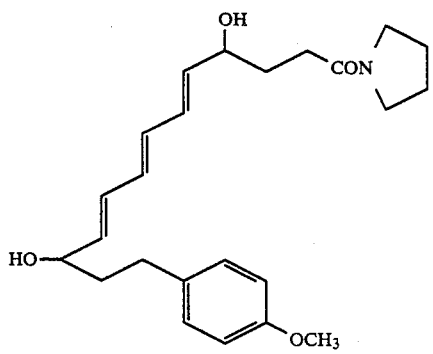

In this article, the authors also suggest that they have found antagonistic activity in a series of unidentified unsaturated dihydroxy fatty acid derivatives which are to be the subject of a future publication.

The pharmacology of the biologically active leukotrienes is generally discussed in J. Clin. Invest. 73, 889-897 (1984).

SUMMARY OF THE INVENTION

This invention encompasses compounds of the formula

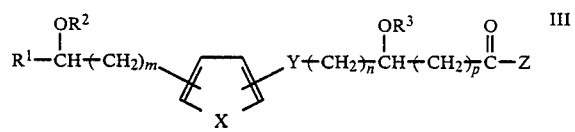

and the pharmaceutically acceptable non-toxic addition salts thereof;

wherein $R^1$ is lower alkyl having 1–10 carbon atoms; lower alkenyl having 2–10 carbon atoms; lower alkynyl and having 2–10 carbon atoms; lower alkadienyl having 3–10 carbon atoms; lower alkadiynyl having 4–10 carbon atoms; or alkenynyl having 4–10 carbon atoms;

wherein $R^2$ and $R^3$ are the same or different and represent hydrogen or lower alkyl having 1–6 carbon atoms;

wherein X is CH=CH, S, or O;

wherein Y is CH=CH or C≡C;

wherein Z is $OR^4$ or $NR^5R^6$, and wherein $R^4$ represents H, lower alkyl having 1–6 carbon atoms, or a pharmaceutically acceptable cation, and wherein $R^5$ and $R^6$ act independently and represent H or lower alkyl having 1–6 carbon atoms, or $R^5$ and $R^6$ may act together with N to form a cycloamine of the formula:

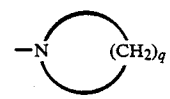

wherein q is an integer from 2–5;

wherein m and n are the same or different and either 1 or 0; and wherein p is an integer from 1 to 5.

DETAILED DESCRIPTION

This invention encompasses compounds of Formula III as previously described. A particularly preferred embodiment of the present invention is encompassed by a compound of the formula:

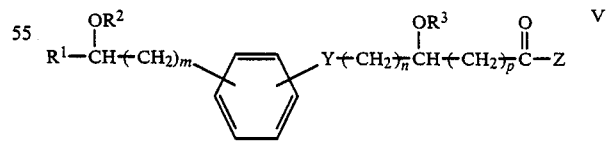

wherein $R^1$, $R^2$, $R^3$, Y, Z, $R^4$, $R^5$, $R^6$, m, n, p, and q are as previously defined for Formulas III and IV.

The term "alkyl" as used to described $R^1$, $R^2$, $R^3$, $R^4$, $R^5$, and $R^6$ means straight or branched chain alkyls having 1–10 carbon atoms.

The term "alkenyl" as used to describe $R^1$ means straight or branched chain alkenyls having 2–10 carbon atoms.

The term "alkynyl" as used to describe $R^1$ means straight or branched chain alkynyls having 2-10 carbon atoms.

The term "alkadienyl" as used to describe $R^1$ means straight or branched chain alkadienes, including allenes, having 3-10 carbon atoms.

The term "alkadiynyl" as used to describe $R^1$ means straight or branched chain alkadiynyls having 4-10 carbon atoms.

The term "alkenynyl" as used to describe $R^1$ means straight or branched chain alkenynyls having 4-10 carbon atoms.

The term "pharmaceutically acceptable cations" as used to describe $R^4$ refers to cations such as ammonium, sodium, potassium, lithium, calcium, magnesium, ferrous, zinc, copper, manganous, aluminum, ferric, manganic, ammonium, tetraalkylammonium, and the like.

The term "pharmaceutically acceptable non-toxic addition salts" refers either to those base derived salts of any compound herein having a carboxylic acid function.

The base derived salts may be derived from pharmaceutically acceptable non-toxic inorganic or organic bases. Among the inorganic bases employed to produce said pharmaceutically acceptable salts are the hydroxide bases of the "pharmaceutically acceptable cations" disclosed above.

Among the organic bases employed to produce said pharmaceutically acceptable salts are the pharmaceutically acceptable non-toxic bases of primary, secondary, and tertiary amines. Especially preferred non-toxic bases are isopropylamine, diethylamine, ethanolamine, dicyclohexylamine, choline, and caffeine.

All the pharmaceutically acceptable non-toxic addition salts are prepared by conventional processes well known to those of ordinary skill in the art.

The compounds of this invention are generally prepared by separately adding two chains to an appropriately substituted aromatic moiety. The first chain can be added by initially performing a nucleophilic addition of a bromoalk-1-yne compound, such as via a Grignard reaction to a bromo-substituted aromatic aldehyde. The aromatic moiety can be phenyl, thienyl or furyl. The Grignard reagent adds to the aldehyde group to form an alkynol compound. The resulting hydroxyl group is typically protected by reaction with a trialkylchlorosilane, preferably t-butyldimethylchlorosilane.

The length of the alkyne side chain can be optionally increased to produce an $R^1$ of the desired length. One method of increasing the chain length is to convert the terminal acetylene into an anion by reaction with an alkyl lithium compound in an aprotic solvent. This anion can then be added to a straight or branched chain alkyl iodide via a nucleophilic substitution. By varying the chain lengths of the bromoalkyne and the iodide compound in the above reaction, the necessary variations can be achieved to produce the $R^1$ substituents claimed in this invention.

The second chain can be added to the above aromatic moiety via a catalytic reaction. By selecting a hydroxyester containing a terminal triple bond and by protecting the hydroxyl group with a trialkylsilane, preferably t-butyldimethylchlorosilane, one can substitute the terminal acetylene for the bromo on the aromatic moiety. By varying the chain length and the position of the hydroxyl group, one can achieve the necessary variations to produce diyne compounds encompassed by the present invention.

The diyne compounds can be catalytically hydrogenated over Lindlar catalyst to produce diene compounds also encompassed by the present invention.

The biological activity possessed by the compounds of this invention was indicated by positive results to the "LTB$_4$ Receptor Binding Assay" and the "Human Neutrophil Degranulation Assay".

PREPARATION OF HUMAN NEUTROPHILS

For use in both the "LTB$_4$ receptor Binding Assay" and the "Human Neutrophil Degranulation Assay", neutrophils were purified from venous blood of normal human donors using standard techniques of dextran sedimentation, centrifugation on Histopaque ® (density solution) and hypotonic lysis of erythrocytes (Boyum, A., *Isolation of Leukocytes From Human Blood: Further Observations*. Scand. J. Lab. Clin. Inves. 21 (Suppl. 97): 31, 1968). The purity of isolated neutrophils was $\geq 95\%$.

LTB$_4$ RECEPTOR BINDING ASSAY

Neutrophils ($4-6 \times 10^6$) in 1 ml of Hanks' balanced salt solution containing 10 mM Hepes Buffer (HBSS), pH 7.4 and 30 $\mu$M nordihydroguaiaretic acid were incubated with 0.6 nM ($^3$H) LTB$_4$ in the presence or absence of test compounds. The incubation was carried out at 0° C. for 45 minutes and terminated by adding 5 ml of ice-cold HBSS followed by rapid filtration of incubation mixture under vacuum through GF/C glass fiber filters. The filters were further washed with 10 ml HBSS and their radioactivity was determined. Specific binding was defined as the difference between total binding and nonspecific binding which was not displaced by $10^{-7}$M unlabeled LTB$_4$.

The inhibition of specific binding was determined for representative compounds of this invention, and the corresponding IC$_{50}$ values calculated (Table 1). An IC$_{50}$ is the concentration of the compound of interest which will inhibit the binding of LTB$_4$ by 50% of the LTB$_4$ receptors. For example, for the compound of Example 7, the IC$_{50}$ was determined to be approximately 5 $\mu$M.

HUMAN NEUTROPHIL DEGRANULATION ASSAY

LTB$_4$ induced neutrophil degranulation was determined by measuring the release of myeloperoxidase activity into the incubation medium. Neutrophils ($3 \times 10^6$) in 1 ml HBSS solution was preincubated with cytochalasin B(5 $\mu$g) at 37° C. for 5 minutes, followed by preincubation with test compounds for 7 minutes. Neutrophils were then incubated for 2 to 20 minutes with either LTB$_4$($5 \times 10^{-8}$M) or the chemotactic peptide f-met-leu-phe ($5 \times 10^6$M) to induce degranulation. Following incubation, samples were centrifuged and myleoperoxidase was extracted from the cell pellets by sonication in phosphate buffer containing 0.4% Triton X-100. Triton X-100 was also added to the supernatents to a concentration of 0.4%. The supernatants and the pellet extracts were then assayed spectrophotometrically for myeloperoxide activity by determining the rate of decomposition of H$_2$O$_2$ with o-dianisidine as hydrogen donor as described by Renlund, D. G., MacFarlane, J. L., Christensen, R. D., Lynch, R. E., and Rothstein, G., *A Quantitative And Sensitive Method For Measurement Of Myeloperoxidose,* Clinical Research 28: 75A, 1980). Myeloperoxidase activity released into the supernatant was expressed as the percent of the average total activity (pellet plus supernatant).

The inhibition of $LTB_4$ induced neutrophil degranulation was determined for representative compounds of this invention and their corresponding $IC_{50}$ values were calculated (Table 1). The concentration of a compound which inhibited $LTB_4$ induced neutrophil degranulation by 50% was determined to be its $IC_{50}$ value.

By virtue of their activity as $LTB_4$ antagonists, the compounds of Formula I are useful in treating inflammatory conditions in mammals such as psoriasis, Crohn's disease, ulcerative colitis and the like. A physician or veterinarian of ordinary skill can readily determine whether a subject exhibits the inflammatory condition. The preferred utility relates to treatment of ulcerative colitis.

The compounds of the present invention can be administered in such oral dosage forms as tablets, capsules, softgels, pills, powders, granules, elixirs, or syrups. The compounds may also be administered intravascularly, intraperitoneally, subcutaneously, intramuscularly, or topically using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, a therapeutically effective amount of one or more compounds of the present invention may be combined with any oral non-toxic pharmaceutically acceptable inert carrier such as lactose, starch, sucrose, cellulose, magnesium stearate, dicalcium phosphate, calcium sulfate mannitol, and the like, or various combinations thereof. For oral administration in liquid forms, such as in softgels, elixirs, syrups, drops and the like, a therapeutically effective amount of the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention may be combined with a suitable carrier such as water, saline, aqueous dextrose, and the like. For topical administration, such as for psoriasis, therapeutically effective amounts of one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds may also be formulated using pharmacologically acceptable base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention are ordinarily in the range of about 1.0 mg/kg up to about 21.0 mg/kg, (preferably in the range of about 2.0 to 14.0 mg/kg (orally)).

The following examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

In the following examples, and throughout this application, a wavey line (∼) defines a substituent as having optional R or S stereochemistry. A broken triangular shape line ( ≡ ) defines the substituent at the base of the triangle as coming out of the plane of the paper, whereas a substituent at the apex of the broken triangle, is defined as going into the plane of the paper.

TABLE 1
Biological Activity For Representative Compounds Of The Invention
| Compound (Example No.) | Structure | Inhibition of Receptor Binding of LTB$_4$ IC$_{50}$(μM) | Inhibition of LTB$_4$ Induced Neutrophil Degranulation IC$_{50}$(μM) |
|---|---|---|---|
| 7 | 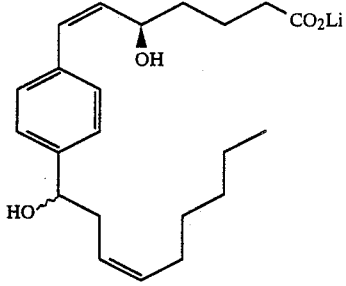 | 5 | 0.7 |
| 12 | 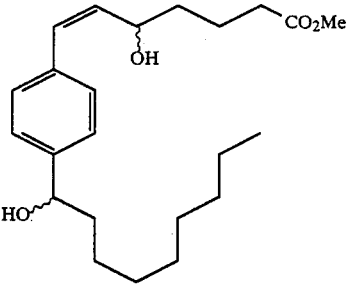 | 1 | 0.65 |
| 21 | 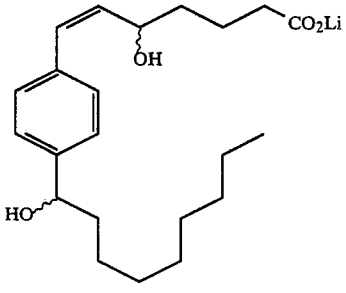 | 2 | 1.0 |
| 23 | 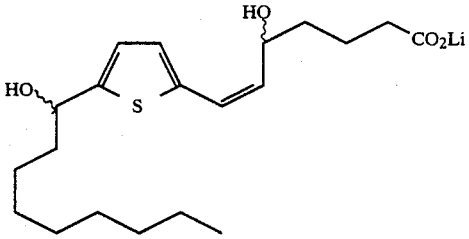 | 5 | 1.8 |
| 22 | 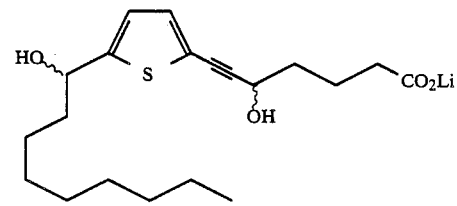 | 20% inhibition at 10μM | 8.7 |

DESCRIPTION OF THE PREFERRED EMBODIMENT

EXAMPLE 1

1-(p-bromophenyl)-but-3-yn-1-ol

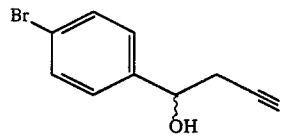

To 4.1 g of flame dried Mg was added 50 ml of diethyl ether ("ether") followed by the addition of a few iodine crystals. To this was added a 10 ml aliquot of a solution continuing 15 ml (168.9 mmol) of propargyl bromide in 50 ml of ether. The reaction was started by the addition of 25 mg of $HgCl_2$. The remaining solution of propargyl bromide in ether was then added at a rate sufficient to maintain a steady reflux. Once addition was complete, the mixture was stirred 1 hour at room temperature (R.T.) and then placed in an ice bath and cooled to 0° C. To the cooled reaction mixture was added dropwise with stirring over a 1 hour period, a solution containing 25 g (135.1 mmol) of 4-bromobenzaldehyde dissolved in 30 ml of ether and 30 ml of THF. Once addition was complete, the ice bath was removed and the reaction mixture stirred overnight at room temperature (R.T.). The reaction was quenched with a saturated $NH_4Cl$ solution. The layers were separated and the aqueous layer was extracted twice with ether. The combined extracts were washed 1× each with $H_2O$, and brine and then dried ($MgSO_4$). Removal of the solvent produced 30.2 g of a crude yellow oil which was semi-purified by high pressure liquid chromatography, HPLC, (silica; gradient elution with methyl t-butyl ether-hexane) to yield 20.8 g of a reaction mixture that was 80% pure in the titled product.

EXAMPLE 2

1-(p-bromophenyl)-1-(t-butyldimethylsiloxy)-3-butyne

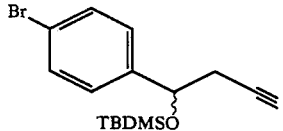

A solution containing 19 g (84.5 mmol) of the semi-purified reaction product of Example 1 dissolved in 50 ml of DMF was cooled to 0° C. (ice bath) and 12.9 g (190 mmol) of imidazole was added in one portion. The reaction mixture was stirred 10 minutes until all the imidazole dissolved and then was added in one portion 14.3 g (95 mmol) of t-butyldimethylchlorosilane. After stirring for 5 minutes, the ice bath was removed and the reaction mixture was stirred for an additional 2 hr. at R.T. The reaction was then poured into 500 ml of ether and washed 3× with 50 cc of $H_2O$ and 1× with 100 ml of brine. The organic layer was then separated, dried ($MgSO_4$), and removal of all solvent yielded 29.32 g of crude product. Separation by reverse phase HPLC (gradient elution with acetonitrile-water) yielded 9.1 g of the titled product.

Analysis for $C_{16}H_{23}OSiBr$ (MW=339.35): Calcd: C, 56.63; H, 6.83; Br, 23.55. Found: C, 56.61; H, 6.88; Br, 23.56.

EXAMPLE 3

1-(p-bromophenyl)-1-(t-butyldimethylsiloxy)-3-nonyne

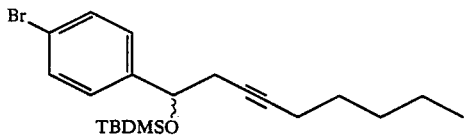

To 2.2 g (63 mmol) of the silylacetylene of Example 2 dissolved in 50 ml of dry THF and cooled to −78° C. under argon was added dropwise 5.6 ml (7.0 mmol) of a 1.25M solution of methyl lithium in diethyl ether. Upon addition, the reaction was warmed to −10° C. and stirred at −10° C. for 30 min. Iodopentane (1.2 ml, 9.0 mmol) was then added followed by 5.0 ml of hexamethylphosphoric triamide (HMPA) whereupon the reaction mixture was warmed to R.T. and stirred overnight. The reaction was quenched with about 5.0 ml of $H_2O$, then poured into hexane and washed 4× with $H_2O$, and 1× with brine. The organic layer was dried ($MgSO_4$) and the solvent removed to yield a dark red oil which was purified by medium pressure liquid chromotography (MPLC) eluting with hexane to yield 2.14 g of the titled product as a pale yellow oil.

1H N.M.R. $\delta_{TMS}$ $CDCl_3$ (300 MHz): −0.08(s, 3H); 0.03(s, 3H); 0.9(s&t, 12H); 1.3(br.m, 4H); 1.43(br.m, 2H); 2.1(tt, 2H); 2.45(m, 2H); 4.72(t, 1H); 7.32(dd, 4H).

EXAMPLE 4

Methyl 7-[4-[1-(t-butyldimethylsiloxy)-3-nonynyl]phenyl]-5S-(t-butyldimethylsiloxy)-6-heptynoate

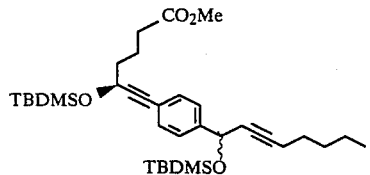

The following reagents were added to a pressure vessel: 0.1 g (0.24 mmol) of 2-(t-butyldimethylsiloxy)-1-p-bromophenyl-3-nonyne, 0.065 g (0.24 mmol) of methyl 5S-(t-butyldimethylsiloxy)-6-heptynoate prepared according to the procedure of Nicolaou et al., J.A.C.S., 106, 2748 (1984) employing the optically active 5S-alcohol, 1 ml of piperidine, and 600 mg (0.005 mole, 2 mole%) of $Pd(PPh_3)_4$. The vessel was degassed with argon, sealed and the reaction mixture was then heated at 100°–120° C. for 2 hr. with stirring. The reaction was then cooled to room temperature, diluted with diethyl ether, filtered, and stripped of all solvent. The residue was purified by MPLC, eluting with 2.5% ethyl acetate-hexane to yield 0.7 g of the titled product.

$^1$H N.M.R. $\delta_{TMS}$ $CDCl_3$ (300 MHz): −0.08(s, 3H); 0.04(s, 3H); 0.15(s, 3H); 0.17(s, 3H); 0.88(s&t, 12H); 0.92(s, 9H); 1.29(m, 4H); 1.43(m, 2H); 1.79(m, 4H); 2.09(tt, 2H); 2.35–2.6(complex, 4H); 3.66(s, 3H); 4.59(t, 1H); 4.74(t, 1H); 7.3(dd, 4H).

EXAMPLE 5

Methyl 7-[4-[1-(t-butyldimethylsiloxy)-3Z-nonenyl]phenyl]-5S-(t-butyldimethylsiloxy)-6Z-heptenoate

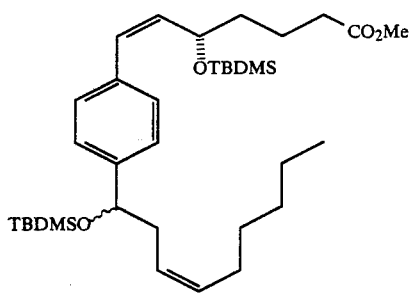

To 0.07 g of the titled product of Example 4 in 10 ml of hexane was added 0.1 ml of quinoline and 10 mg of Lindlar catalyst. The mixture was stirred under a $H_2$ atmosphere for 7 hours at room temperature. The reaction was recharged with an additional 10 mg of catalyst and the reaction was permitted to run overnight. The reaction mixture was filtered through Celite ® (diatomaceous earth) and the filtrate was evaporated to give an oil. Purification by MPLC eluting with 2.5% ethyl acetate-hexane produced 0.060 g of the title product.

$^1$H N.M.R. $\delta_{TMS}$ CDCl$_3$ (300 MHz): −0.15(s, 3H); −0.1(s, 3H); 0.02(s, 3H); 0.05(s, 3H); 0.85(s, 9H); 0.9(s&t, 12H); 1.28(br.m, 4H); 1.55–1.9(br.m, 6H); 1.96(m, 2H); 2.34–2.6(br.m&t, 4H); 3.7(s, 3H); 4.65(m, 2H); 5.40(m, 2H); 5.65(dd, 1H); 6.44(d, 1H); 7.2(dd, 4H).

EXAMPLE 6

Mixture of

Methyl 7-[4-(1-hydroxy-3Z-nonenyl)phenyl]5S-hydroxy-6Z-heptenoate and

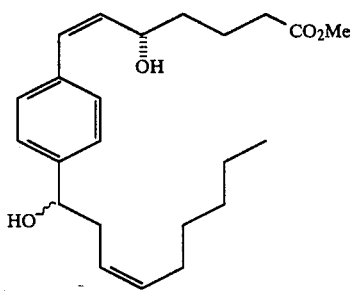

Tetrahydro-6S-[2-[4-(1-hydroxy-3Z-nonenyl)phenyl]-Z-ethenyl]-2H-pyran-2-one

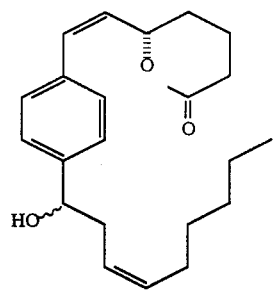

To 0.32 g (0.53 mmol) of the product of Example 5 dissolved in 0.5 ml of DMF was added 6.4 mg (2.1 eq.) of KF, 1.4 mg (0.1 eq.) of 18-crown-6-polyether, and 2 µl (2.1 eq.) of $H_2O$. The reaction was stirred under Ar for 24 hr. An additional 6 mg of KF was then added and the reaction was stirred overnight at R.T. The reaction mixture was then poured into water and the aqueous solution extracted 3× with ether. The combined extracts were washed 2× with $H_2O$ and 2× with brine and dried (MgSO$_4$). Removal of the solvent in vacuo produced an oil. The oil was purified by flash chromatography (silica, gradient elution with ether-petroleum ether). Fraction I contained 0.00247 g (0.0066 mmol) of the ester (A). Fraction II contained 0.00166 g (0.0049 mmol) of the lactone (B). Fraction III contained an additional 0.00609 g of the ester and lactone in a 1:4 ratio (determined by $^1$H N.M.R.).

Lactone:
$^1$H N.M.R. $\delta_{TMS}$ CDCl$_3$ (300 MHz): 0.88(t, 3H); 1.27(m, 6H); 1.7–2.1(complex, 5H); 2.4–2.7(complex, 4H); 4.63(t, 1H); 5.16(m, 1H); 5.3–5.65(m, 2H); 5.22(dd, 1H); 6.2(d, 1H); 7.33(dd, 4H).

Ester:
$^1$H N.M.R. $\delta_{TMS}$ CDCl$_3$ (300 MHz): 0.89(t, 3H); 1.25(m, 6H); 1.6–1.8(m, 4H); 2.02(m, 2H); 2.35(t, 2H); 2.4–2.64(m, 4H); 3.68(s, 3H); 4.58(m, 1H); 4.71(t, 1H); 5.4(m, 1H); 5.58(m, 1H); 5.66(dd, 1H); 6.55(d, 1H); 7.3(dd, 4H).

EXAMPLE 7

7[4-(1-hydroxy-3Z-nonenyl)phenyl]-5S-hydroxy-6Z-heptenoic acid, lithium salt

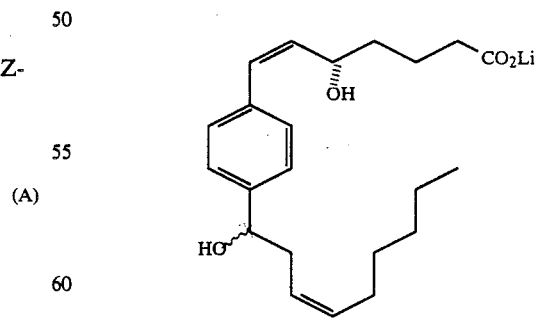

The combined ester and lactone products (0.017 mmol) of Example 6 were dissolved in 0.3 ml of methanol and cooled to 0° C. Upon dissolution, 0.1 ml of $H_2O$ was added followed by 20 µl (0.02 mmol) of a 1M LiOH solution. The slurry was stirred for five minutes and then warmed to room temperature. After 24 hrs, an additional 5 μl of 1M LiOH was added and stirring continued for an additional 24 hours. The reaction mixture was then evaporated to dryness under a stream of N₂ and the last traces of solvent were removed under high vacuum. The reaction produced 6.2 mg of the titled product.

¹H N.M.R. $\delta_{d4Na\text{-}TSP}$ D₂O (300 MHz): 5.2–5.5(m, 2H); 5.63(dd, 1H); 6.07(d, 1H); 7.3(dd, 4H).

EXAMPLE 8

Methyl 7-[4-(1-hydroxy-3-nonynyl)phenyl]-5S-hydroxy-6-heptynoate

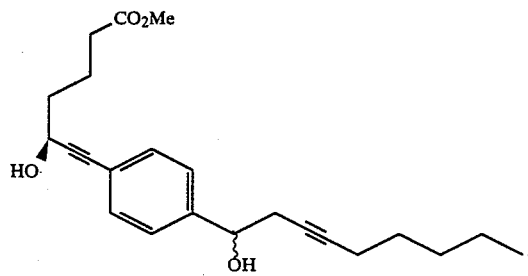

To 0.044 g (0.074 mmol) of the product of Example 4 was added 0.3 ml (0.3 mmol) of 1M tetra-n-butyl-ammonium fluoride in tetrahydrofuran (THF) with stirring at room temperature. The reaction mixture was stirred 6 hours at room temperature and then poured into brine. The brine, containing the reaction mixture, was then extracted 5× with diethyl ether and dried (MgSO₄). The dried reaction mixture was then stripped of all solvent and the residue was taken up in 10 ml of methanol. To the methanol solution was added 2 mg of sodium methoxide and the reaction was stirred overnight. The reaction was stripped in vacuo to give an oil. The oil was purified by flash chromatography (silica; gradient elution with ether-petroleum ether) to give 5 mg of the titled product.

¹H N.M.R. $\delta_{TMS}$ CDCl₃ (300 MHz): 0.9(t, 3H); 1.3(m, 4H); 1.48(m, 2H); 1.65(broad s, 1H); 1.85(m, 4H); 2.15(m, 3H); 2.42(t, 2H); 2.5–2.65(m, 2H); 3.59(s, 3H); 4.61(broad s, 1H); 4.8(t, 1H); 7.87(dd, 4H).

EXAMPLE 9

7-[4-(1-hydroxy-3-nonynyl)phenyl]-5S-hydroxy-6-heptynoic acid, lithium salt

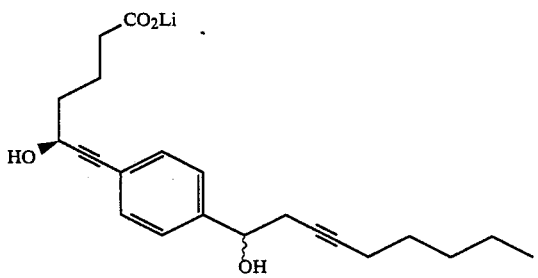

The titled product was prepared according to the reaction described in Example 7, employing 5 mg (0.0135 mmol) of the product of Example 8 instead of the product of Example 6. The reaction was run until thin layer chromatography (TLC) indicated that all starting material was consumed. The yield was 4.9 mg of titled material.

EXAMPLE 10

1-(p-bromophenyl)-1-nonanol

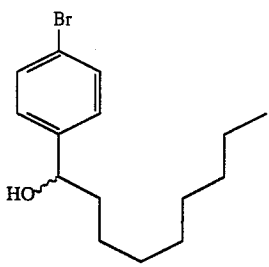

In a 100 ml round bottom flask with a Y-adapter, condensor, and a 10 ml addition funnel was added 0.38 g (15.63 mmol) of Mg turnings which had been ground with a mortar and pestle. The apparatus was then flushed with argon and flamed dried. After allowing the apparatus to cool under argon, 4 ml of anhydrous diethyl ether was added to the Mg. While vigorously stirring the Mg in the ether, 2.52 g (13.05 mmol) of 1-bromooctane in 3 ml of diethyl ether was added dropwise. After 5 drops, the Grignard reaction started and the addition was continued at a rate sufficient to maintain a steady reflux. After addition was complete, 4 ml of dry THF was added to the Grignard reagent and it was stirred at R.T. for an additional ½ hour. A warm water bath was then placed under the flask, and refluxing was continued for 15 minutes. Afterwards, the reaction was cooled to 0° C. with an ice bath and 2.00 g (16.81 mmol) of p-bromobenzaldehyde in 4 ml of THF was added. The reaction was stirred at R.T. for 1.5 hr., whereupon the Grignard was quenched with saturated NH₄Cl. The organic layer was washed with H₂O and brine, then dried (MgSO₄). Rotary evaporation of the solvent under reduced pressure produced 2.96 g of a crude yellow oil. The oil was dissolved in a diethyl ether and loaded onto a silica gel column. Elution with diethyl ether/hexane yielded 2.22 g of the titled product as a yellow oil.

Analysis for C₁₅H₂₃OBr (MW=299.26): Calcd: C, 60.20; H, 7.75. Found: C, 60.46; H, 7.87.

EXAMPLE 11

Methyl 7-[4-(hydroxynonyl)phenyl]-5-hydroxy-6-heptynoate

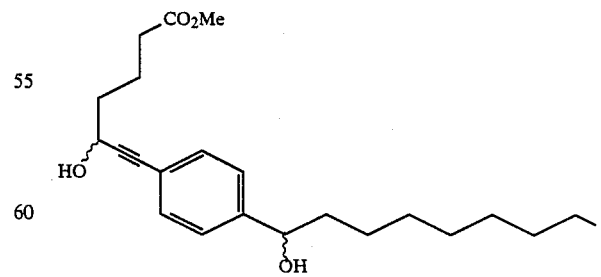

Into a heavy walled pyrex tube was added 102 mg (0.34 mmol) of 1-p-bromophenyl)-1-nonanol, 53 mg (0.34 mmol) of methyl 5-hydroxy-6-heptynoate prepared according to the procedure of Nicolaou et al., J.A.C.S., 106, 2748 (1984), 10 mg (0.009 mmol, 2.5 mole%) of Pd(PPh$_3$)$_4$, and 2 ml (1.4 g) of diisopropylamine. The tube was degassed with argon, sealed and placed in a hot oil bath at approximately 100° C. After about 40 min., a white solid fell out of solution. The reaction was monitored by TLC over the next four hours—some halide was still present, but the acetylene disappeared. The reaction was allowed to cool to R.T. and 40 ml of ether was added. The ether solution was extracted with H$_2$O and brine and then dried (MgSO$_4$). The solvent was stripped from the dried organic phase leaving 100 mg of a yellow oil. The oil was taken up in ether and chromatographed on a silica gel column eluting with 30% diethyl ether/hexane to produce 40 mg of the titled product of a yellow oil.

$^1$H N.M.R. $\delta_{TMS}$ CDCl$_3$ (300 MHz): 7.40(d, 2H); 7.28(d, 2H); 4.57–4.73(broad m, 2H); 3.69(s, 3H); 2.43(broad t, 2H); 2.12(broad d, 1H); 1.10–1.95(broad m, 19H); 0.88(broad t, 3H).

EXAMPLE 12

Methyl 7-[4-(1-hydroxynonyl)phenyl]-5-hydroxy-6Z-heptenoate

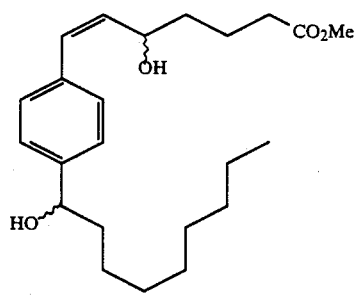

To 2 ml of hexane in a 10 ml round bottom flask was added 38 mg of the titled product of Example 11. The mixture was stirred and benzene was added until the oil went into solution. Upon dissolution, 8 mg of Lindlar catalyst and 0.1 ml of quinoline were added. The flask was evacuated, flushed 5× with H$_2$, and then stirred under a H$_2$ balloon for 3 days. TLC showed that starting material was still present and an additional 8 mg of Lindlar catalyst was added. After 24 hr. there was almost no starting material remaining. Ether (3 ml) was added to the reaction mixture and it was filtered through Celite ® (diatomaceous earth.) The reaction mixture was then sequentially washed with H$_2$O and brine and then dried (MgSO$_4$). Upon removal of the solvent under reduced pressure, the yellow oil residue was chromatographed on a silica gel column slurry packed in 70% diethyl ether/hexane. The titled product was recovered as an oil.

Analysis for C$_{23}$H$_{36}$O$_4$ (MW=376.52): Calcd: C, 73.36; H, 9.64. Found: C, 73.10; H, 9.80.

$^1$H N.M.R. $\delta_{TMS}$ CDCl$_3$ (300 MHz): 7.33(d, 2H); 7.25(d, 2H); 6.55(d, 1H); 5.65(dd, 1H); 4.67(broad t, 1H); 4.58(broad t, 1H); 3.67(s, 3H); 2.35(broad t, 2H); 1.20–1.90(broad m, 20H); 0.87(broad t, 3H).

EXAMPLE 13

1-(o-bromophenyl)-1-nonanol

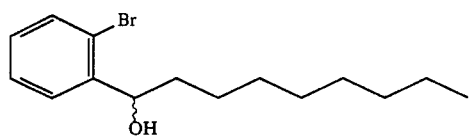

The titled product was prepared according to the procedure of Example 10 substituting o-bromobenzaldehyde for p-bromobenzaldehyde.

EXAMPLE 14

Methyl 7-[2-(1-hydroxynonyl)phenyl]-5-hydroxy-6-heptynoate

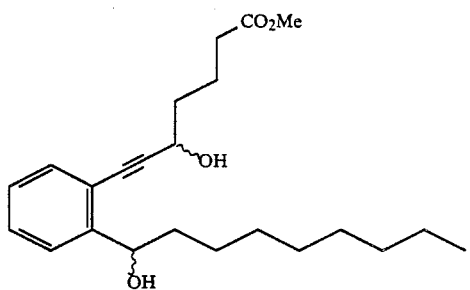

Into a heavy walled pyrex test tube was added 130 mg (0.43 mmol) of 1-(0-bromophenyl)-1-nonanol, 67 mg (0.43 mmol) of methyl 5-hydroxy-6-heptynoate prepared according to the procedure of Nicolaou et al., J.A.C.S., 106, 2748 (1984), 25 mg (0.02 mmol, 5 mole%) of Pd(PPh$_3$)$_4$, and 4 ml (93.0 mg) of diisopropylamine. The reaction was run and worked up according to the procedure of Example 11 to yield 208 mg of a yellow-brown oil. The oil was chromatographed on a silica gel column which was eluted with 70% diethyl ether/hexane to produce the titled product as a yellow oil.

$^1$H N.M.R. $\delta_{TMS}$ CDCl$_3$ (300 MHz): 7.18–7.55(m, 4H); 5.12(broad t, 1H); 4.65(m, 1H); 3.69(s, 3H); 2.44(broad t, 2H); 1.1–2.30(broad m, 20H); 0.87(broad t, 3H).

EXAMPLE 15

1-[2-(5-bromo)furanyl]-1-nonanol

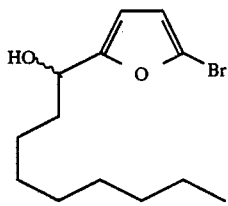

To 0.099 g (4.07 mmol) of pulverized Mg turnings in 5 ml of diethyl ether (in an apparatus set up as in Example 10) was added dropwise with stirring 0.68 g (3.52 mmol) of 1-bromooctane in 10 ml of diethyl ether. After stirring for ¼ hour, the reaction mixture was cooled in an ice bath and 20 ml of THF was then added. To the reaction mixture was added dropwise with stirring 0.50 g (2.86 mmol) of 5-bromo-2-furancarboxaldehyde in 20 ml of THF. After the addition was complete, the reaction mixture was stirred for an additional 2 hr. at R.T. The reaction was quenched with saturated NH₄Cl and the organic layer was sequentially extracted with H₂O and brine and then dried (MgSO₄). Upon removal of the solvent by rotary evaporation at reduced pressure, 0.79 g of a brown oil remained. The oil was chromatographed on silica gel, eluting with 25% ethyl acetate/hexane, to yield 0.50 g of the titled product as a yellow oil.

Analysis for $C_{13}H_{21}O_2Br$ (MW=289.21): Calcd: C, 53.98; H, 7.32. Found: C, 54.34; H, 7.17.

EXAMPLE 16

Methyl 7-[2-[5-(1-hydroxynonyl)]furanyl]-5-hydroxy-6-heptynoate

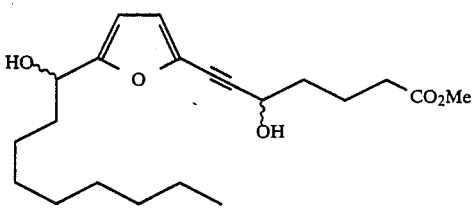

In a heavy walled pyrex test tube containing 3 ml (2.2 g) of diisopropylamine was added 29 mg (0.10 mmol) of the titled product of Example 15, 16 mg (0.10 mmol) of methyl-5-hydroxy-6-heptynoate prepared according to the procedure of Nicolaou et al., J.A.C.S., 106, 1748 (1984), and 9 mg (0.008 mmol, 8 mole%) of Pd(PPh₃)₄. The reaction was run and worked up according to the procedure of Example 11 to yield a yellow-brown oil. Chromatography of the oil on a silica gel column eluted with 70% diethyl ether/hexane yielded the titled product as a yellow oil.

¹H N.M.R. $\delta_{TMS}$ CDCl₃ (300 MHz): 6.52(d, 1H); 6.22(d, 1H); 4.63(broad m, 2H); 3.68(s, 3H); 2.35-2.45(broad t, 2H); 1.10-2.13(broad m, 20H); 0.88(broad t, 3H).

EXAMPLE 17

Methyl 7-[2-[5-(1-hydroxynonyl)]furanyl]-5-hydroxy-6Z-heptenoate

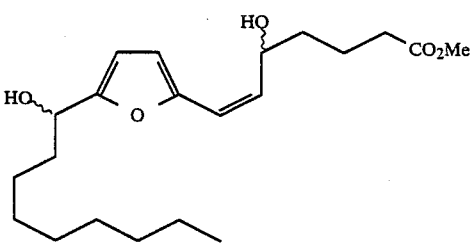

To 16.1 mg (0.044 mmol) of the titled product of Example 16, was added 3 mg of Lindlar catalyst and 15 μl of quinoline. The reaction vessel was then flushed 5× with H₂ and the reaction mixture was stirred under a H₂ balloon for 1 hour. Afterwards, the reaction mixture was worked up as in Example 12 to produce a crude yellow oil. The oil was chromatographed on silica gel column which was eluted with 40% ethyl acetate/hexane to yield 13 mg of the titled product as a yellow oil.

¹H N.M.R. $\delta_{TMS}$ CDCl₃ (300 MHz): 6.25(s, 2H); 6.15(d, 1H); 5.55(dd, 1H); 5.00(broad t, 1H); 4.65(broad t, 1H); 3.69(s, 3H); 2.40(broad t, 2H); 1.10-1.90(broad m, 20H); 0.87(broad t, 3H).

EXAMPLE 18

1-[2-(5-bromo)thienyl]-1-nonanol

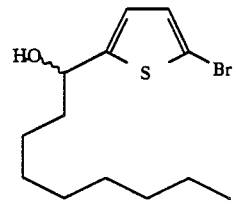

In a 500 ml 3-necked round bottom flask equipped with a condensor and a 250 ml addition funnel was added 1.66 g (68.28 mmol) of Mg. Under a steady flow of argon, the apparatus was flamed. Upon cooling to R.T., 25 ml of diethyl ether was added to the Mg turnings, followed by the dropwise addition of 12.21 g (63.22 mmol) of 1-bromooctane with vigorous stirring. The Grignard started quickly and addition was continued at a dropwise rate sufficient to maintain steady reflux. After the addition was complete, the reaction was stirred for 1 hr. and 100 ml of freshly distilled THF was added to the Grignard which was then cooled in an ice bath. To the cooled Grignard reagent was added 10.00 g (52.34 mmol) of 5-bromo-2-thiophenecarboxaldehyde. The reaction mixture was worked up according to the procedure in Example 10. The resulting brown-yellow oil was chromatographed on a silica gel column. Elution with 20% diethyl ether/hexane produced 9.51 g of the titled product as a yellow oil.

Analysis for $C_{13}H_{21}BrOS$ (MW=305.27): Calcd: C, 51.14; H, 6.93; Br, 26.18. Found: C, 51.35; H, 6.94; Br, 26.03.

EXAMPLE 19

Methyl 7-[2-[5-(1-hydroxynonyl)]thienyl]-5-hydroxy-6-heptynoate

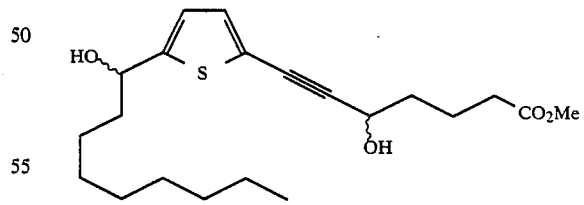

To 30 ml of diisopropylamine in a heavy walled pyrex test tube was added 283 mg (0.93 mmol) of the titled product from Example 18, 143 mg (0.92 mmol) of methyl 5-hydroxy-6-heptynoate prepared according to the procedure of Nicolaou et al., J.A.C.S., 106, 2748 (1984), and 43 mg (0.04 mmol, 4 mole%) of Pd(PPh₃)₄. The reaction was run and worked up according to the procedure of Example 11. Chromatography of the resulting oil on silica gel column, which was eluted with 75% diethyl ether/hexane, yielded 66 mg of the purified titled product was a yellow oil.

$^1$H N.M.R. $\delta_{TMS}$ CDCl$_3$ (300 MHz): 7.05(d, 1H); 6.80(d, 1H); 4.85(t, 1H); 4.60(broad t, 1H); 3.68(s, 3H); 2.40(broad t, 2H); 2.15-2.30(m, 2H); 1.70-1.90(m, 6H); 1.20-1.40(m, 12H); 0.88(broad t, 3H).

EXAMPLE 20

Methyl 7-[2-[5-(1-hydroxynonyl)]thienyl]-5-hydroxy-6Z-heptenoate

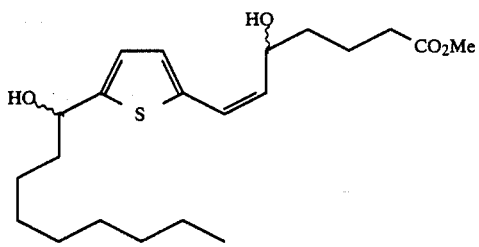

To 42 mg of the titled product of Example 19 was added 4 mg of 9.5% Lindlar catalyst and 15 μl of quinoline. The reaction vessel was flushed 5× with H$_2$ and then stirred under a H$_2$ balloon overnight. An additional 3 mg of catalyst was added and the reaction stirred as above for an additional 3 hours. The reaction mixture was diluted with 10 ml of diethyl ether and filtered through Celite ® (diatomaceous earth). The filtrate was washed with H$_2$O and brine and then dried (MgSO$_4$). Evaporation of the solvent under reduced pressure produced a crude yellow oil. The oil was chromatographed on a silica gel column, which was eluted with 80% diethyl ether/hexane. The resulting titled product was isolated as a yellow oil.

$^1$H N.M.R. $\delta_{TMS}$ CDCl$_3$ (300 MHz): 6.85(broad s, 2H); 6.53(d, 1H); 5.55(dd, 1H); 4.87(m, 2H); 3.68(s, 3H); 2.38(broad t, 2H); 1.17-2.00(broad m, 20H), 0.87(broad t, 3H).

Analysis for C$_{21}$H$_{34}$O$_4$S (MW=382.55): Calcd: C, 65.93; H, 8.96. Found: C, 65.93; H, 9.15.

EXAMPLE 21

7-[4-(1-hydroxynonyl)phenyl]-5-hydroxy-6Z-heptenoic acid, lithium salt

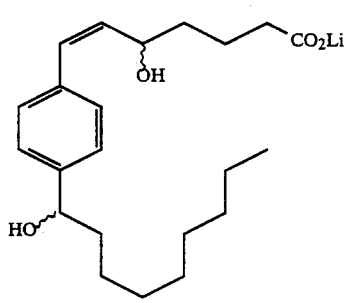

The titled product was prepared according to the reaction described in Example 7 employing the product of Example 12 instead of the product of Example 6. The reaction was run until TLC indicated that all the starting material was consumed.

EXAMPLE 22

7-[2-[5-(1-hydroxynonyl)]thienyl-5-hydroxy-6Z-heptynoic acid, lithium salt

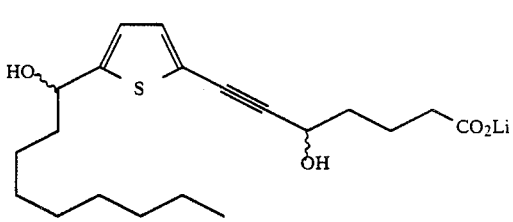

The titled product was prepared according to the reaction described in Example 7 employing the product of Example 19 instead of the product of Example 6. The reaction was run until TLC indicated that all the starting material was consumed.

EXAMPLE 23

7-[2-[5-(1-hydroxynonyl)]thienyl-5-hydroxy-6Z-heptenoic acid, lithium salt

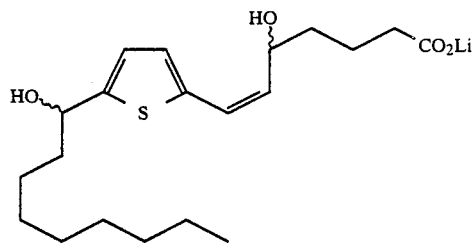

The titled product was prepared according to the reaction described in Example 7 employing the product of Example 20 instead of the product of Example 6. The reaction was run until TLC indicated that all the starting material was consumed.

What is claimed is:

1. A compound of the formula:

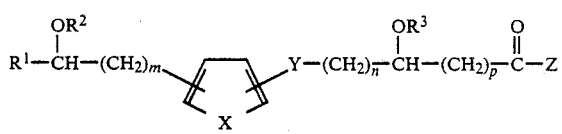

and the pharmaceutically acceptable addition salts thereof; wherein R$^1$ is lower alkyl having 1-10 carbon atoms; lower alkenyl having 2-10 carbon atoms; lower alkynyl having 2-10 carbon atoms; lower alkadienyl having 3-10 carbon atoms; lower alkadiynyl having 4-10 carbon atoms; or alkenylyl having 4-10 carbon atoms;

wherein R$^2$ and R$^3$ are the same or different and represent hydrogen or lower alkyl having 1-6 carbon atoms;

wherein X is CH=CH, S, or O;

wherein Y is CH=CH or C≡C;

wherein Z is OR$^4$ or NR$^5$R$^6$, and wherein R$^4$ represents H, lower alkyl having 1-6 carbon atoms, or a pharmaceutically acceptable cation, and wherein R$^5$ and R$^6$ independently represent H or lower alkyl having 1-6 carbon atoms, or wherein R$^5$ and R$^6$ together with N form a cycloamine of the formula:

wherein q is an integer from 2-5;
wherein m and n are the same or different and either 1 or 0; and
wherein p is an integer from 1 to 5.

2. A compound according to claim 1 wherein X is CH=CH.

3. A compound according to claim 1 of the formula:

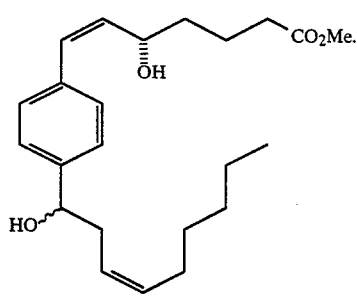

4. A compound according to claim 1 of the formula:

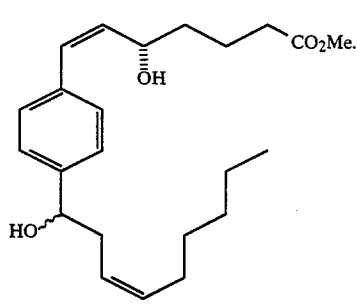

5. A compound according to claim 1 of the formula:

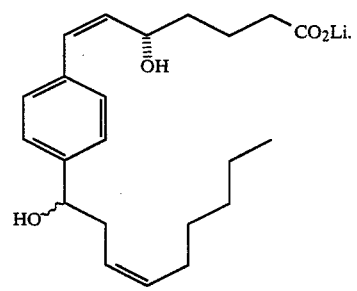

6. A compound according to claim 1 of the formula:

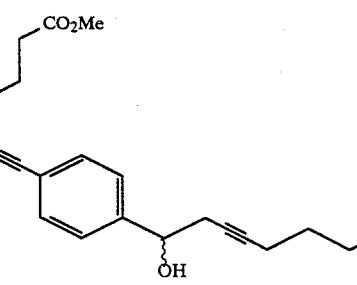

7. A compound according to claim 1 of the formula:

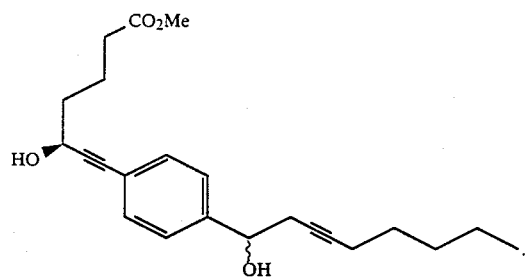

8. A compound according to claim 1 of the formula:

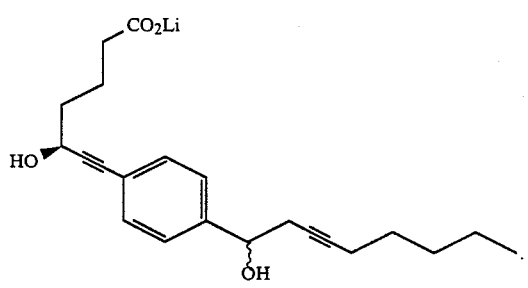

9. A compound according to claim 1 of the formula:

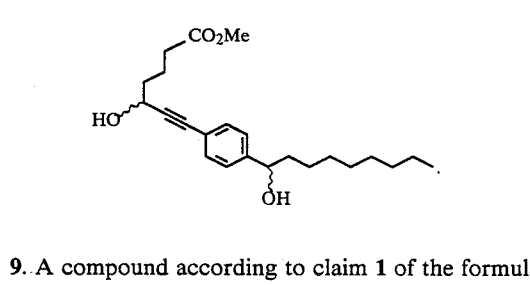

10. A compound according to claim 1 of the formula:

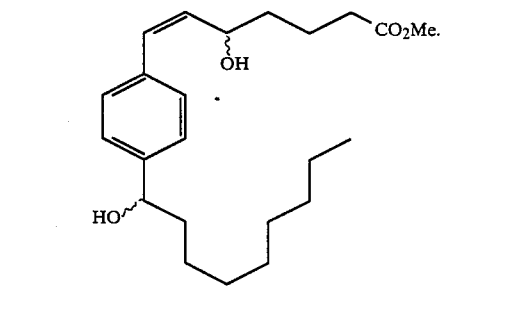

11. A compound according to claim 1 of the formula:

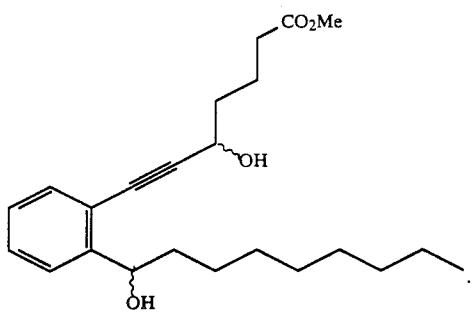

12. A compound according to claim 1 of the formula:

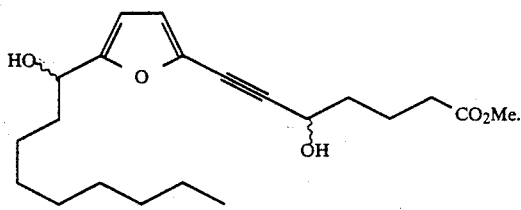

13. A compound according to claim 1 of the formula:

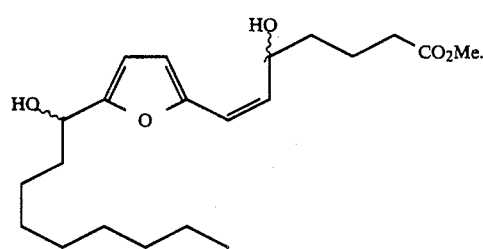

14. A compound according to claim 1 of the formula:

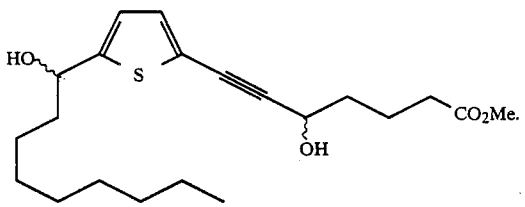

15. A pharmaceutical composition comprising a compound according to claim 1 and a non-toxic pharmaceutically acceptable carrier.

16. A pharmaceutical composition according to claim 15 wherein said compound is of the formula:

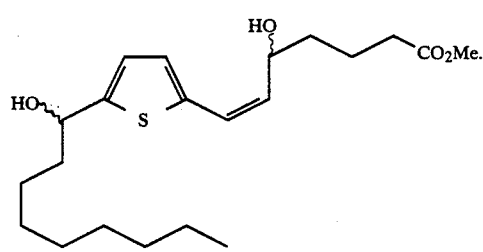

17. A pharmaceutical composition according to claim 15 wherein said compound is of the formula:

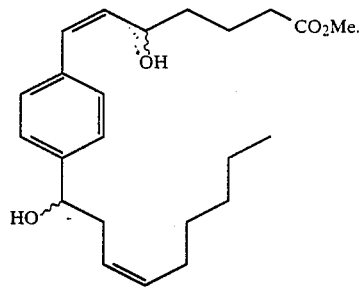

18. A pharmaceutical composition according to claim 15 wherein said compound is of the formula:

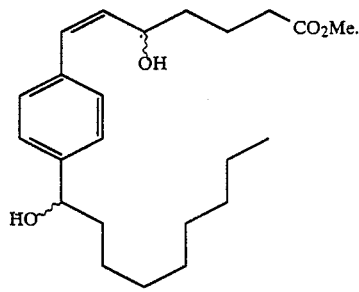

19. A pharmaceutical composition according to claim 15 wherein said compound is of the formula:

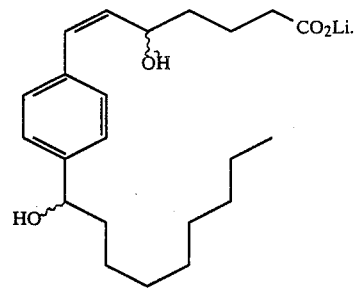

20. A pharmaceutical composition according to claim 15 wherein is in oral unit dosage form.

21. A method of treating an inflammatory condition in mammals comprising administering a non-toxic therapeutically effective amount of a compound according to claim 1 to a mammal in need of such treatment.

22. A method of treatment according to claim 21 wherein said inflammatory condition is ulcerative colitis.

23. A method of treatment according to claim 21 wherein said inflammatory condition is Crohn's disease.

24. A method of treatment according to claim 21 wherein said inflammatory condition is psoriasis.

* * * * *

UNITED STATES PATENT AND TRADEMARK OFFICE
CERTIFICATE OF CORRECTION

PATENT NO. : 4,791,133

DATED : December 13, 1988

INVENTOR(S) : Djuric, et al.

It is certified that error appears in the above-identified patent and that said Letters Patent is hereby corrected as shown below:

Column 6, lines 64-65, reading "A broken triangular shape line (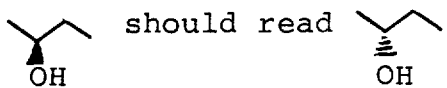)" should read -- A broken triangular shape line ( ) --.
Column 7, the first structure, that portion of the structure reading 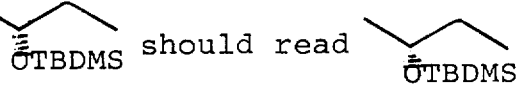 should read
Column 9, the second structure, Example 2, the following definition has been omitted and should be included: -- TBDMSO = t-butyldimethylsiloxy --.
The above Correction also applies to Column 10, the first structure, Example 3.
Column 10, line 55, reading "600 mg" should read -- 6mg --.
Column 11, the first structure, Example 5, that portion of the structure reading 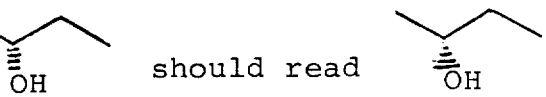 should read
Column 11, the second structure, Example 6, that portion of the structure reading 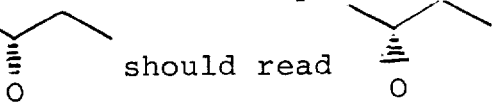 should read
Column 12, the first structure, Example 6, that portion of the structure reading should read
Column 12, the second structure, Example 7, that portion of the structure reading 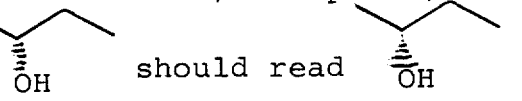 should read Column 21, the second structure, Claim 3, that portion of the

UNITED STATES PATENT AND TRADEMARK OFFICE
CERTIFICATE OF CORRECTION

PATENT NO. : 4,791,133
DATED : December 13, 1988
INVENTOR(S) : Djuric, et al.

It is certified that error appears in the above-identified patent and that said Letters Patent is hereby corrected as shown below:

structure reading 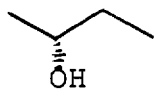 should read 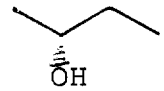

Column 21, the third structure, Claim 4, that portion of the structure reading 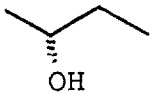 should read 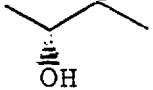

Column 24, the first structure, Claim 16, that portion of the structure reading 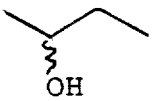 should read 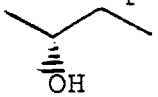

Column 24, line 58, Claim 20, reading "wherein" should read -- which --.

Signed and Sealed this

Ninth Day of October, 1990

Attest:

HARRY F. MANBECK, JR.

Attesting Officer    Commissioner of Patents and Trademarks